United States Patent [19]

Eubanks

[11] Patent Number: Plant 6,906

[45] Date of Patent: Jul. 4, 1989

[54] CORN PLANT NAMED SUN DANCE

[75] Inventor: Mary W. Eubanks, Raleigh, N.C.

[73] Assignee: Vanderbilt University, Nashville, Tenn.

[21] Appl. No.: 117,096

[22] Filed: Nov. 4, 1987

[51] Int. Cl.[4] ..... A01H 5/00

[52] U.S. Cl. ..... Plt./89

[58] Field of Search ..... Plt./89

*Primary Examiner*—Robert E. Bagwill

*Attorney, Agent, or Firm*—Tilton, Fallon, Lungmus and Chestnut

[57] ABSTRACT

A new variety of a corn plant distinguished by its drouth resistance, multiple types of inflorescence, bifurcated styles and profuse production of fruit, with up to five to ten ears being on one stem or culm.

3 Drawing Sheets

BACKGROUND OF THE NEW PLANT

Maize (*Zea mays L.*) is one of mankind's most important food crops. Maize is also the only major cultivated plant for which there is no documented wild ancestor and no conclusive evidence concerning its origin, until now. In 1979, a previously unknown relative of maize, a perennial grass at the threshold of extinction, was found in the mountains near Jalisco, Mexico, by Iltis, et al. *Science* vol. 203, 186–188. This grass, diploid perennial teosinte (*Zea diploperennis*) is in the same genus as maize, has the same chromosome number (n=10), and hybridizes easily with it.

*Tripsacum dactyloides* is a more distant relative of corn with a different chromosome number (n=18). It had been known to hybridize with maize but not with teosinte. During the 1984 field season in Bloomington, Ind., I made crosses using pollen from *Tripsacum dactyloides* onto diploperennis and obtained normal looking fruits. Hybrids were selected for propagation for their drouth resistance, profuse fruit production and because they appeared to be the natural bridge to place Tripsacum genes in teosinte, thereby establishing a link between wild grasses and corn plants as we know them today. Unique propagation of this plant through successive generations by means of cutting has demonstrated that the new plant has not only retained the continuous and abundant production capability but also that its distinguishing characteristics hold true from generation to generation and appeared to be firmly fixed. Propagation has taken place at Bloomington, Ind., Nashville, Tenn., and Raleigh, N.C.

DESCRIPTION OF THE DRAWINGS

My new corn plant is illustrated by the accompanying full color photographic drawing, which shows a fully grown plant, including the narrow long leaf, as well as tassels and fruit.

DESCRIPTION OF THE NEW PLANT

The following is a detailed description of my new corn plant based upon observations of plants grown under conventional greenhouse procedures and in the field.

THE PLANT

Origin: Seedling.

Parentage:

*Seed parent.*—*Zea diploperennis.*

*Pollen parent.*—*Tripsacum dactyloides.*

Classification:

*Botanic.*—*Zea indiana* (proposed).

Habit: Essentially erect; as many as 15 primary culms, usual number about 5–10.

Duration:

*Perennial.*—Sends out shoots from a rhizome system. Plant will freeze at temperature below 28° F.

Culm:

*Height.*—Up to two meters; slender, simple with occasional branching from upper nodes; glabrous; oval in cross section; diameter 1–1.5 cm.

*Nodes.*—glabrous, aerial roots develop at nodes along entire culm.

*Sheath.*—tightly closed enwrapping the culm, margins not united; glabrous; turns red when exposed to sun, otherwise green; red, ciliate auricles at summit margins.

*Ligule.*—present on adaxial side of leaf at junction of blade and sheath; length: 4 mm; membranaceous, irregular edge.

Leaf blade: Alternate; distichous; sheathing base; parallel veined; narrowly linear, flat, thin.

*Length.*—56–47 cm. Width: 1.5–5.0 cm.

*Entire margin.*—Red, serrulate.

*Midrib.*—White.

*Adaxial surface.*—Sparsely hirsute.

*Abaxial surface.*—Glabrous.

*Prominent parallel veins.*—4 per 1 cm width.

INFLORESCENCE

Blooming period: Twice annually for approximately one month beginning in late April and late October in Indiana, Tennessee and North Carolina.

Monoecious: Separate male and female flowers on the same plant; variable.

Staminate flowers: May be of two types: one inflorescence type born as paired spikelets on a slender rachis forming 9–10 racemes arranged in a panicle, the "tassel", at the summit of the culm.

*Length.*—15–20 cm. Alternatively, staminate spikelets may be borne on a single spike above the pistillate flowers.

*Axis.*—stiff, continuous, ascending.

Spikelet: Two-flowered, one sessile, one pediceled; Laterally compressed awnless, attenuate with red tip and red band at base; Length: 9 mm; Width: 2 mm. In pairs on one side of a persistent central axis.

*Pedicel length.*—3 mm.

*Glumes.*—membranous, flat, several nerved.

Pistillate flowers: Borne in leaf axils; spikelets distichously arranged; variable. One type of pistillate flower consists of a single rowed spike of 4 to 6 triangular caryopses in hard, shell-like fruitcases enclosed in a single leaf sheath; caryopses disarticulate upon maturity. Length: 7 mm; Width: 5 mm. Color: pale to white or pale with brown speckles. Alternatively, spikelets paired and partially enclosed in stiff, brown speckled glumes; caryopses rounded and imbricate; Spikes enclosed in single or multiple leaf sheaths. Caryopses do not disarticulate upon maturity; Length: 5 mm; Width: 5 mm. Color: golden orange Styles: red, puberulent, bifucated tip: Length: 5–8 cm.

Fruit: Five to ten ears per culm per blooming period; flowers are produced twice a year; some plants may produce approximately 100 ears twice annually.

Maturity: 45 days following fertilization.

Color: Most kernels are R.H.S. 159 C with shadings of R.H.S. 202.

COMPARATIVE PARENTAL CHARACTERISTICS

A. Ear (Husked Ear Data Unless Stated Otherwise)

Length: About 51 mm.

Midpoint diameter: About 5.3 mm.

Weight: About 0.6 gm.

Kernel rows: 2 (rarely 3–4).

Silk color (exposed at silking stage): White, initially, then turns pink.

Husked color: Cob kernels are embedded in the rachis segments that disarticulate upon maturity. These segments are brownish gray and resemble kernels, however, they are not actual kernels.

Kernal color: Light brown.

Husked extension (harvest stage): About 1 cm.

Shank: About 6.5 cm.

Taper: Slight.

Position in dry husk stage: Upright.

Drying time (unhusked ear): About 2–3 days.

B. Kernel (Dried)

Size (from midpoint): Length about 3.9 mm, Width about 2.8 mm, Thickness about 2.7 mm.

Shape grade (% round): 100% round (tip pointed).

Pericarp color: Brown.

Aleurone color: Clear.

Endosperm color: White.

Endosperm type: Pop.

Weight 20 seeds (unsized samples): About 0.4 gm.

C. Cob

Diameter at midpoint: About 5.3 mm.

Strength: Poor.

Color: Brownish Gray.

Culm: *Zea diploperennis* round in cross section; diam. 1 cm. *Tripsacum dactyloides* oval in cross section; diam. 1.3 cm.

Leaf blade: *Z. diploperennis.* Width 1–2 cm; margins pink serrulate from midsection of blade to tip; adaxial surface: sparsely hirsute; prominent veins: 6 per 1 cm width. *T. dactylodies* Width: 1 cm; margins white serrulate along entire blade; Adaxial surface: hirsute; prominent veins: 12 per 1 cm width.

Blooming period: *Z. diploperennis* twice a year, end of March and end of September for about a month. *T. dactyloides* continously from May to October.

Staminate flowers: *Z. diploperennis* borne in tassel at summit of culm *T. dactyloides* staminate flowers borne above pistillate flowers in single spike.

Pistillate flowers: *Z. diploperennis* caryopsis triangular in hard bony fruitcases; Length 8 mm; Width: 4 mm; color: black, dark brown or brown speckled. *T. dactyloides* caryopsis trapezoidal in hard, bony fruitcase; Length: 6–8 mm; color: pale brown.

I claim:

1. A new and distinct variety of corn plant, substantially as herein shown and described characterized by its profuse production of fruit, multiple types of inflorescence, bifurcated styles and resistance to drouth.

* * * * *

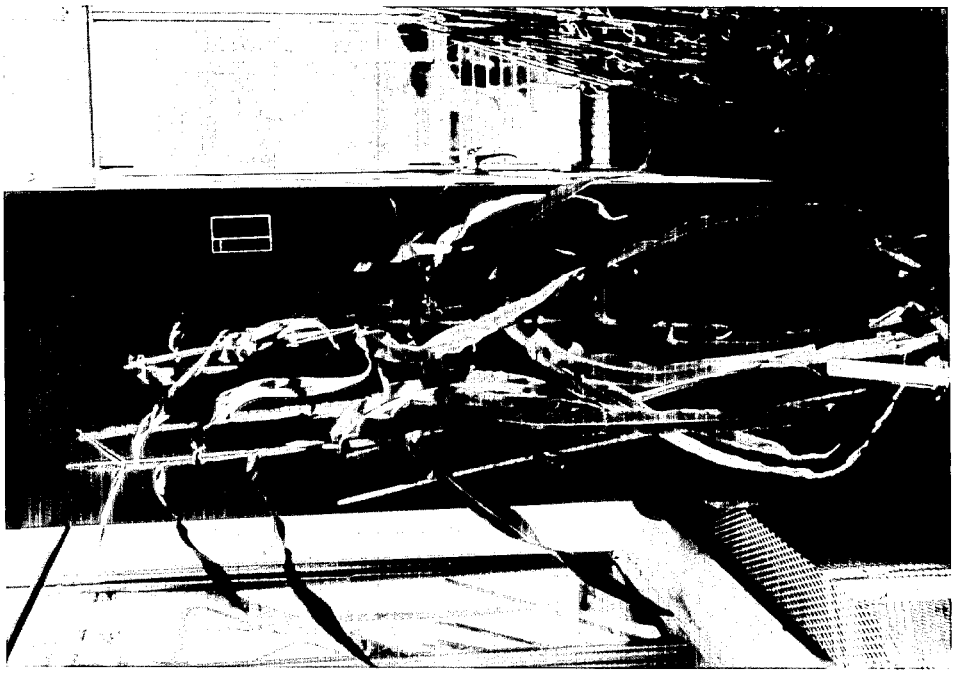
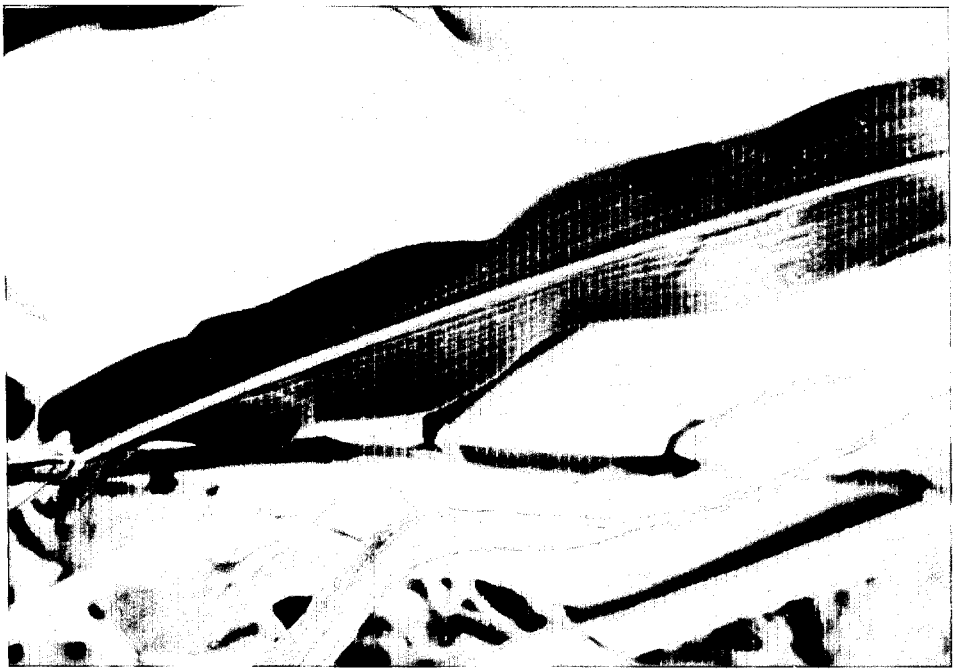

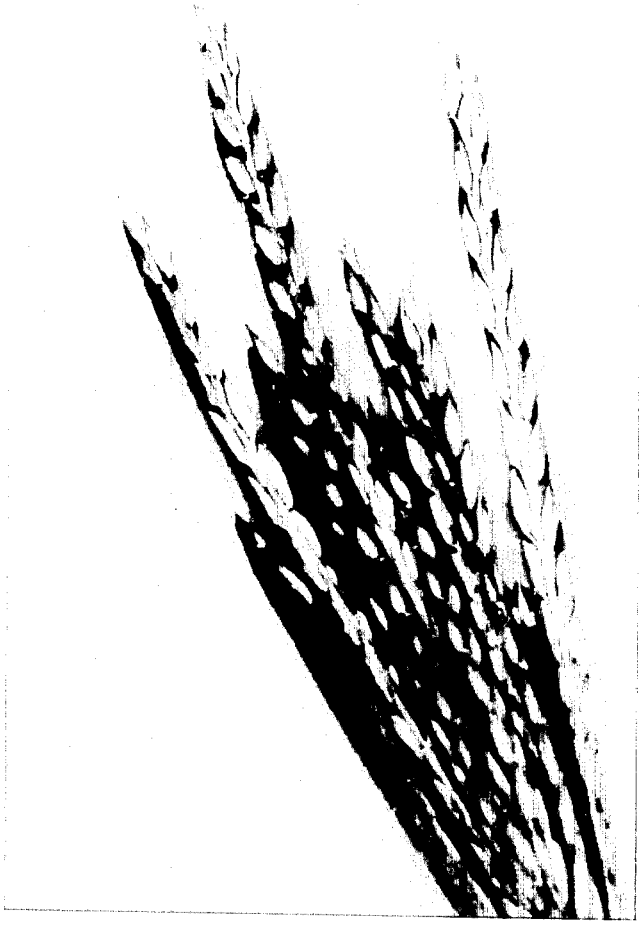

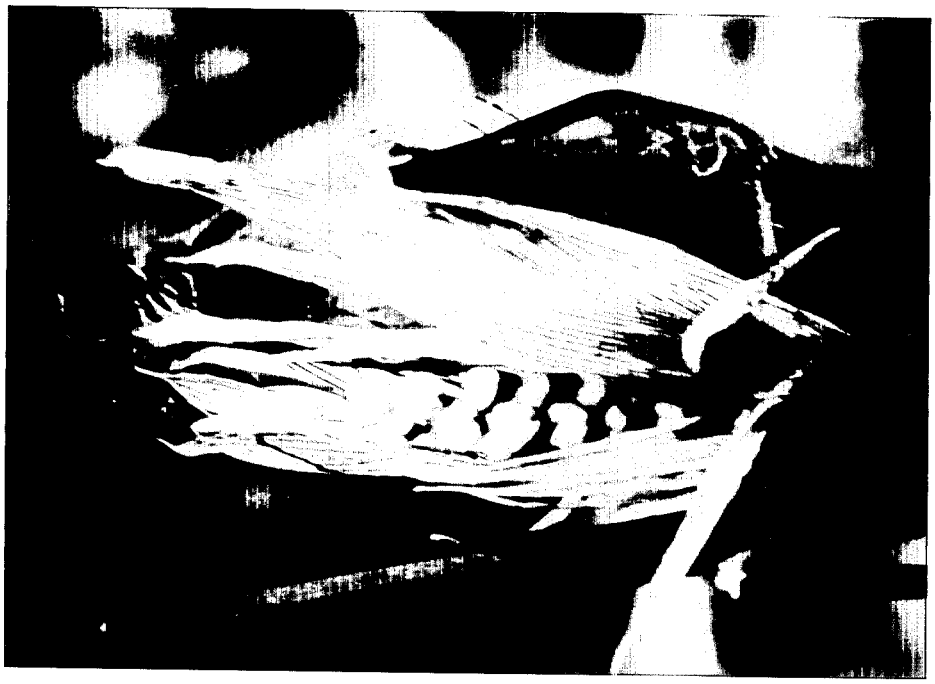
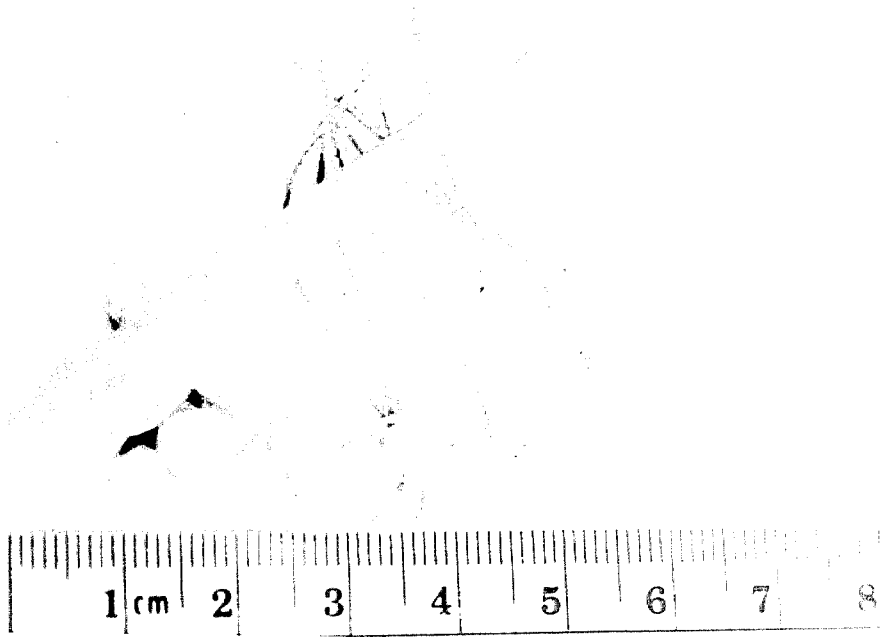
1 cm 2 3 4 5 6 7 8